United States Patent [19]

Nulty

[11] Patent Number: 5,045,149
[45] Date of Patent: Sep. 3, 1991

[54] METHOD AND APPARATUS FOR END POINT DETECTION

[75] Inventor: James E. Nulty, San Jose, Calif.

[73] Assignee: VLSI Technology, Inc., San Jose, Calif.

[21] Appl. No.: 542,811

[22] Filed: Jun. 22, 1990

Related U.S. Application Data

[63] Continuation of Ser. No. 261,780, Oct. 24, 1988, abandoned.

[51] Int. Cl.⁵ .............................................. H01L 21/00
[52] U.S. Cl. ...................................... 156/627; 156/653; 156/657; 156/662; 156/345; 204/192.33; 204/298.32; 356/222; 356/437
[58] Field of Search ............... 156/627, 626, 345, 653; 156/657, 662; 204/192.33, 298.32; 356/222, 437

[56] References Cited

U.S. PATENT DOCUMENTS

| | | | |
|---|---|---|---|
| 4,198,261 | 4/1980 | Busta et al. | 156/626 |
| 4,289,188 | 9/1981 | Mizutani et al. | 156/626 |
| 4,312,732 | 1/1982 | Degenkolb et al. | 204/192 |
| 4,332,833 | 6/1982 | Aspnes et al. | 427/8 |
| 4,377,436 | 3/1983 | Donnelly et al. | 156/626 |
| 4,405,989 | 9/1983 | Tsukada et al. | 364/525 |
| 4,430,151 | 2/1984 | Tsukada | 156/626 |
| 4,479,848 | 10/1984 | Otsubo et al. | 156/626 |
| 4,491,499 | 1/1985 | Jerde et al. | 156/626 |
| 4,493,745 | 1/1985 | Chen et al. | 156/626 |
| 4,496,425 | 1/1985 | Kuyel | 156/626 |
| 4,569,592 | 2/1986 | Osada et al. | 356/318 |
| 4,602,981 | 7/1986 | Chen et al. | 156/627 |
| 4,611,919 | 9/1986 | Brooks et al. | 356/357 |
| 4,657,620 | 4/1987 | Davis et al. | 156/345 |
| 4,695,700 | 9/1987 | Provence et al. | 219/121 PD |

Primary Examiner—David A. Simmons
Assistant Examiner—Thi Dang
Attorney, Agent, or Firm—Limbach, Limbach & Sutton

[57] ABSTRACT

A method and an apparatus for detecting the endpoint in a plasma etching process is disclosed. The invention uses a positive filter and a negative filter simultaneously to generate a first and a second signal respectively. The first and second signals are combined to form a combined signal. A change in the combined signal is indicative of the endpoint.

10 Claims, 2 Drawing Sheets

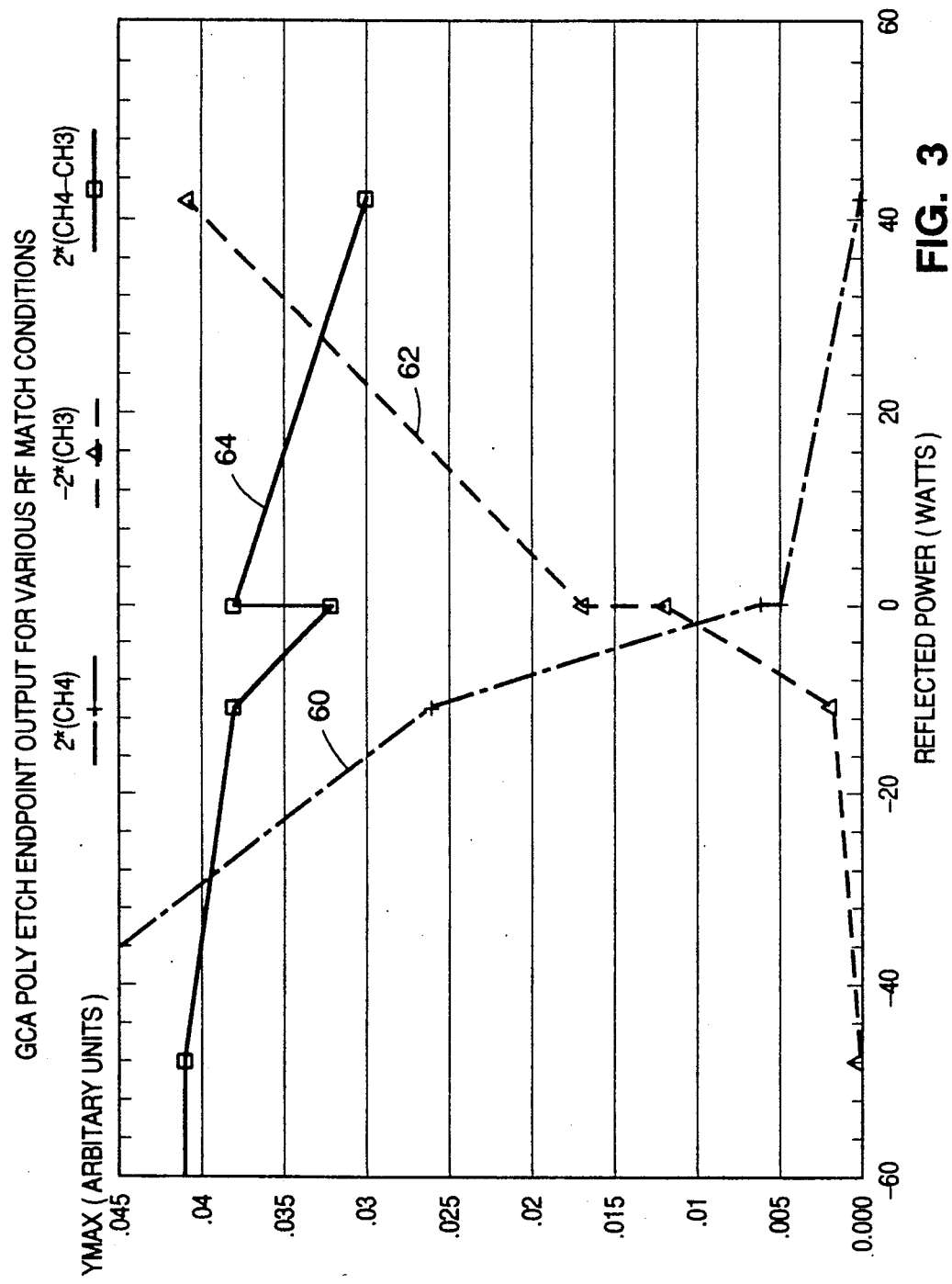

METHOD AND APPARATUS FOR END POINT DETECTION

This is a continuation of application Ser. No. 07/261,780, filed Oct. 24, 1988, now abandoned.

TECHNICAL FIELD OF THE INVENTION

The present invention relates to a method and to an apparatus for detecting the end point of a plasma etching process, which is the time at which the plasma etching process should be terminated. More particularly, the present invention relates to an improved method and apparatus using a positive filter and a negative filter simultaneously to detect the end point.

BACKGROUND OF THE INVENTION

The etching of silicon wafers by "plasma" or "dry etch" technique is well known in the art. A silicon wafer comprises a layer of a first material on top of a layer of a second different material, with certain portions of the first material exposed to the plasma through a mask. The wafer is subjected to the plasma etching process. The aim of the plasma etching process is to etch away the first material until the second material is exposed without etching any of the second material. Thus, a critical factor is to determine when the plasma etching process should terminate.

One of the prior art methods for monitoring the etching of a silicon wafer is to monitor the amplitude intensity of the optical emission from the plasma discharge. Many processes have particular spectra lines or regions which are driven by the presence of some chemical constituents in the plasma such as a reactant species or a plasma etch product produced as an etching by-product. By monitoring the intensity at the wave length of these species in the plasma, the concentration of those species in the plasma, which is directly related to the status of the etching process, can be determined.

Recognizing, however, that the monitoring of a single spectra line does not necessarily result in the exact determination of when the second material has been completely etched away exposing the first material, another prior art method teaches the monitoring of a narrow band centered about a predetermined spectra line which is indicative of the gas phase concentration of the plasma etch reactant or product of the plasma, and a wide band centered about a predetermined spectra line indicative of the optical background emission signal. Other art describes adding a reference filter to the main signal filter which compensates for changes in the plasma due to things other than film clearing. The drawback of this method is that it assumes a non-zero main filter output signal; this is not always the case. Because the change in the RF match at the end point can artifically dampen or strengthen a single end point filter output, the drawback of the prior art technique is that they have not been highly reproducible.

SUMMARY OF THE INVENTION

In this present invention, a method and apparatus is disclosed for determining the end point time at which a plasma etching process should be terminated. The plasma etching process etches a first material over a second different material. The optical emission intensity of the plasma etch process is monitored by a positive filter generating a first signal in response thereto. Simultaneously, the optical emission intensity of the plasma etch process is monitored by a negative filter generating a second signal in response thereto. The first signal is combined with the second signal to produce a combined signal. The combined signal is detected for a change wherein the change is indicative of the first material being etched away exposing the second different material.

BRIEF DESCRIPTION OF THE DRAWINGS

FIG. 3 is a graph of reflected power versus optical emission intensity detected by the use of a positive filter, a negative filter, and combining the signals of the positive and the negative filter.

DETAILED DESCRIPTION OF THE DRAWINGS

Figure 1:
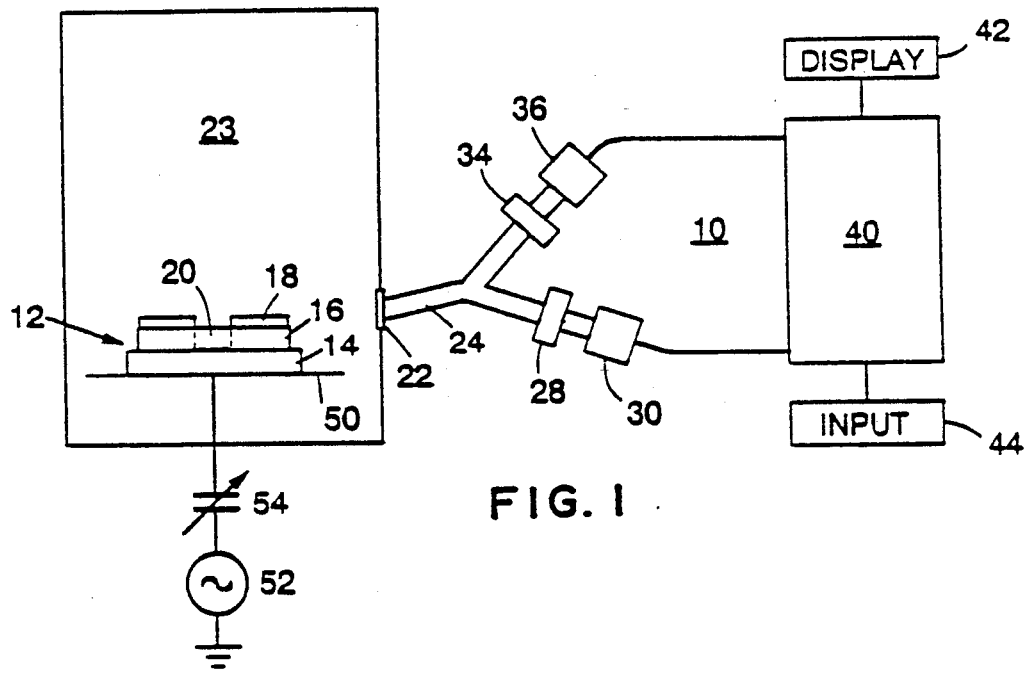
FIG. 1 is a schematic diagram of an apparatus of the present invention.

Referring to FIG. 1 there is shown a schematic diagram of an apparatus 10 of the present invention. The apparatus 10 is suitable for monitoring the plasma etching of a silicon wafer 12. The wafer 12 comprises a first material 16 on a second different material 14. A mask 18 covers the first material 16 selectively exposing the first material 16 to the plasma. In the plasma etching process, the plasma etches away the first material 16 until it reaches the second material 14. The amount of first material 16 etched away is designated as 20.

The apparatus 10 is a radio frequency powered plasma etching device. Thus, the second material 14 is in direct contact with a first electrode 50. An RF generator 52 generates radio-frequency power which is supplied to the electrode 50 through a variable capacitor 54.

The apparatus 10 of the present invention is suitable for determining when the first material 16 has been etched away to expose the second material 14, thereby terminating the etch process. The apparatus 10 is connected to a quartz lens 22 of the plasma chamber 23. A fiber optic cable 24 links the lens 22 to a positive filter 28 and onto a first photomultiplier tube 30. The first photomultiplier tube 30 generates a first signal which is supplied to a controller 40 such as a computer. The fiber optic cable 24 also links the quartz lens 22 to a negative filter 34 onto a second photomultiplier tube 36. The second photomultiplier tube 36 generates a second signal which is also supplied to the controller 40. The controller 40 has an input 44 thereto and an output display 42.

In the operation of the apparatus 10 of the present invention, power is supplied to the plasma chamber 23 to generate the plasma which begins to etch away the first material 16 through the exposed region in the mask 18. The intensity of the optical emission produced within the plasma chamber 23 is detected simultaneously by both the first and second photomultiplier tubes 30 and 36, after receiving them through the positive and negative filters 28 and 34, respectively. By a positive filter, it is meant a filter which generates a signal which generates an increase in signal amplitude upon the detection of the first material 16 being etched away. Similarly, by a negative filter, it is meant a filter which generates a signal which is a decrease in signal amplitude upon the detection of the first material 16 being etched away.

The first and second signals supplied to controller 40 are combined by the controller 40 to produce a combined signal. The controller 40 monitors the combined signal and detects when there is a change in the combined signal. When there is a change in the combined signal, the change is representative of the etching process having etched away the first material 16 to expose the second material 14. The time at which the combined signal is changed, is the time to stop the etching process.

Figure 2:
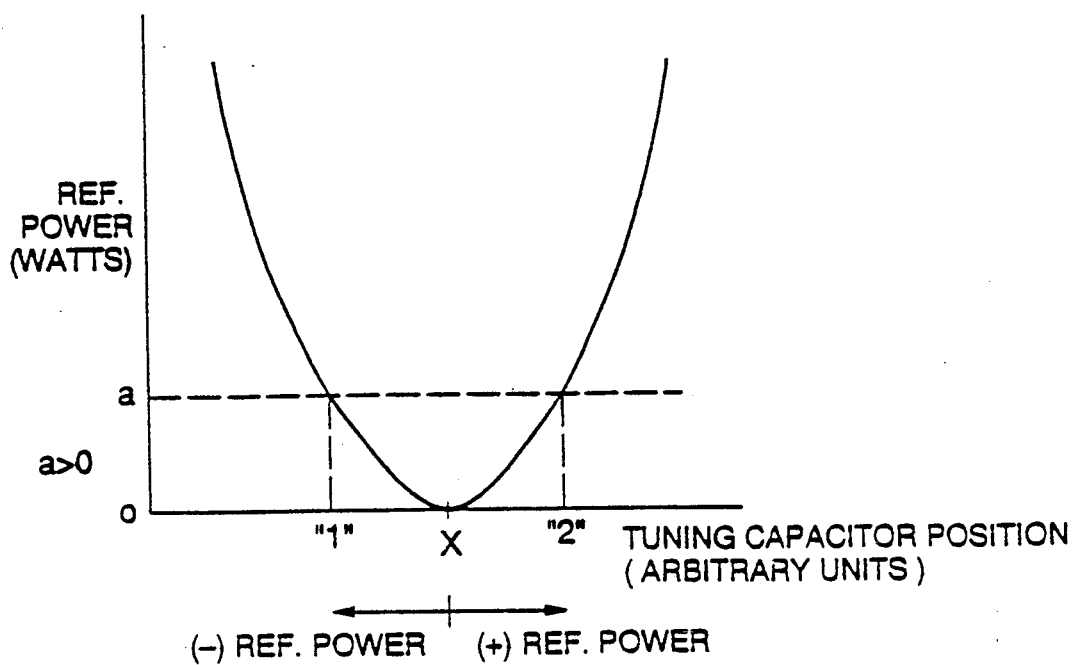
FIG. 2 is a graph of reflected power output of the apparatus of the present invention versus tuning position of the variable capacitor.

The theoretical basis for the present invention can be understood by referring to FIGS. 2 and 3. FIG. 2 shows the power reflected from the electrode 50 as a function of the tuning position of the capacitor 54. The total RF power supplied to the apparatus 10 is approximately the power output of the RF generator 52 minus the reflected power from the electrode 50. Thus, to maximize the power supplied to the apparatus 10, it is desirable to minimize the power reflected from the electrode 50. However, due to electronics drift, etc., it is often not possible to minimize the reflected power. As can be seen from FIG. 2, other than the minimal position "x", there are two positions: match condition "1" and match condition "2" which result in the same power output. Typical RF matching networks do not distinguish between these two match conditions.

It has been discovered that the power output condition(s) are important in the determination of when the process should be terminated. In particular, it has been discovered that using a single filter alone, e.g., a positive filter, for RF match condition "1" (refer to FIG. 2), the filter may generate a strong, detectable change signal upon the completion of etching of the first material 16. However, for RF match condition "2" (refer to FIG. 2 also, which shows that match condition "1" and match condition "2" result in the same power output), the same filter may generate a weak or substantially non-detectable change signal. This results in non-reproducible endpoint signals. In the present invention, a positive filter is used where the positive filter generates a detectable change signal at match condition "1" and a substantially weak signal at match condition "2". A negative filter is used where the negative filter generates a detectable change signal at match condition "2" and a substantially weak signal at match condition "1". By combining the output of the positive filter with the inverse of the output of the negative filter, a combined signal is produced, which generates a detectable change signal, irrespective of RF match conditions. This can be seen by the following table.

TABLE 1

| RF Match Condition | Pos. Filter Signal | Neg. Filter Signal | Pos. − Neg. Signal |
|---|---|---|---|
| 1 | strong (+) | weak or zero | strong (+) |
| 2 | weak or zero | strong (−) | strong (+) |

FIG. 3 shows the graph of a second signal 60 which is the output of the second photomultiplier tube 36 detecting the optical emission intensity of the plasma through the negative filter 34. Channel 3 or Ch3 is the output of the negative filter 34. As can be seen in FIG. 3, the output signal is strong for minus-reflected power, but weak for positive-reflected power. Thus, for the same reflected power, the output signal is depended upon the RF match condition.

Similarly, FIG. 3 shows a graph of a first signal 62 generated by the first photomultiplier tube 30 detecting the optical emission intensity of the plasma through the positive filter 28. Channel 4 or Ch4 is the output of the positive filter 28. First signal 62 is also dependent on RF match condition.

However, as can be seen in FIG. 3, by combining the first signal 60 and the second signal 62 to produce combined signal 64, the combined signal 64 is relatively stable over all reflected power range. Thus, the method of the present invention using both positive and negative filters to create a single endpoint output results in a reproducible endpoint signal which is insensitive to the RF match condition.

One example of the method of the present invention is in the etching of polysilicon which is deposited on silicon dioxide. The positive filter is chosen to detect a spectral line at 280±15 nm. The negative filter 28 is chosen to detect a spectral line at 475±135 nm. The photomultiplier tubes and the controller 40 are of conventional design and are supplied by GCA Corp. The result is substantially that which is shown in FIG. 3.

What is claimed is:

1. A method of determining a time at which a radio frequency powered plasma etching process, etching a first material over a second different material, should be terminated when the first material is etched away exposing the second different material, wherein the method comprising the steps of:

monitoring an optical emission intensity of said plasma etch process by a positive filter, a filter which generates a signal which increases in signal amplitude upon the detection of the first material being etched away, generating a first signal in response thereto, said first signal varying in intensity depending upon the etching process;

simultaneously monitoring the optical emission intensity of said plasma etch process by a negative filter, a filter which generates a signal which decreases in signal amplitude upon the detection of the first material being etched away, generating a second signal in response thereto, said second signal varying in intensity depending upon the etching process;

combining said first signal with said second signal to produce a combined signal; and detecting a change in said combined signal, wherein said change is indicative of said first material being etched away exposing said second different material.

2. The method of claim 1 wherein said first material is a polysilicon.

3. The method of claim 1 wherein said second different material is silicon dioxide.

4. The method of claim 1, wherein said positive filter monitors said emission intensity in the frequency range of approximately 280±15 nm.

5. The method of claim 1, wherein said negative filter monitors said emission intensity in the frequency range of approximately 477±135 nm.

6. The method of claim 1, wherein said combining step comprises the first signal subtracting the second signal.

7. An apparatus for determining a time at which a plasma etching process, etching a first material over a second different material, should be terminated when the first material is etched away exposing the second different material, said apparatus having means for generating said plasma, wherein the improvement comprising positive filter means for monitoring an optical emission intensity of said plasma etch process, and for generating a first signal in response thereto, said first signal varying in intensity depending upon the etching process and increasing in signal amplitude upon the detection of the first material being etched away;

negative filter means for simultaneously monitoring the optical emission intensity of said plasma etch process, and for generating a second signal in response thereto, said second signal varying in intensity depending upon the etching process and decreasing in signal amplitude upon the detection of the first material being etched away;

means for combining said first and second signals to produce a combined signal; and means for detecting a change in said combined signal, wherein said change is indicative of said first material being etched away exposing said second different material.

8. The apparatus of claim 4 wherein said positive filter means is adapted to generate a signal in response to the detection of optical emission intensity in the frequency range of approximately 280±15 nm.

9. The apparatus of claim 4 wherein said negative filter means is adapted to generate a signal in response to the detection of optional emission intensity in the frequency range of approximately 477±135 nm.

10. The method of determining a time at which a radio frequency powered plasma etching apparatus, etching a first material over a second different material, should be terminated when the first material is etched away exposing the second different material wherein the radio frequency powered plasma etching apparatus has two settings for generating substantially the same amount of power output, wherein the method comprising the steps of:

monitoring an optical emission intensity of said plasma etching process by a first filter generating a first output signal therefrom, said first output signal varying in intensity depending upon the etching process, wherein upon the exposure of the second material, said first output signal increases in signal amplitude and is a first detectable signal at said first setting of said apparatus, and said first output signal is a substantially undetectable signal at said second setting of said apparatus;

simultaneously monitoring the optical emission intensity of said plasma etching process by a second filter generating a second output signal therefrom, said second output signal varying in intensity upon the etching process wherein upon the exposure of the second material, said second output signal decreases in signal amplitude and is a second detectable signal at said second setting of said apparatus, and said second output signal is a substantially undetectable signal at said first setting of said apparatus;

combining said first and second output signals of said first and second filters; and detecting a change in said combined signal, wherein said change is indicative of said first material being etched away exposing said second different material.

* * * * *